US009272967B2

(12) United States Patent
Wang et al.

(10) Patent No.: US 9,272,967 B2
(45) Date of Patent: Mar. 1, 2016

(54) PROCESS FOR PRODUCING 1-CHLORO-3,3,3-TRIFLUOROPROPENE IN AN IONIC LIQUID

(71) Applicant: Honeywell International Inc., Morristown, NJ (US)

(72) Inventors: Haiyou Wang, Amherst, NY (US); Hsueh Sung Tung, Getzville, NY (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 14/507,914

(22) Filed: Oct. 7, 2014

(65) Prior Publication Data

US 2015/0105596 A1 Apr. 16, 2015

Related U.S. Application Data

(60) Provisional application No. 61/891,184, filed on Oct. 15, 2013.

(51) Int. Cl.
*C07C 17/25* (2006.01)
*C07C 17/20* (2006.01)

(52) U.S. Cl.
CPC ............... *C07C 17/206* (2013.01); *C07C 17/25* (2013.01); *C07B 2200/09* (2013.01)

(58) Field of Classification Search
CPC .............................. C07C 17/206; C07C 17/25
See application file for complete search history.

(56) References Cited

U.S. PATENT DOCUMENTS

| | | | |
|---|---|---|---|
| 4,140,719 | A | 2/1979 | Tull et al. |
| 5,710,352 | A | 1/1998 | Tung |
| 6,403,847 | B1 | 6/2002 | Nakada et al. |
| 6,844,475 | B1 | 1/2005 | Tung et al. |
| 2010/0191025 | A1 | 7/2010 | Perdrieux |
| 2010/0237279 | A1 | 9/2010 | Hulse et al. |
| 2011/0201853 | A1 | 8/2011 | Tung et al. |
| 2011/0218369 | A1 | 9/2011 | Elsheikh et al. |
| 2011/0218370 | A1 | 9/2011 | Elsheikh et al. |
| 2012/0059199 | A1 | 3/2012 | Pokrovski et al. |
| 2013/0041190 | A1 | 2/2013 | Pigamo et al. |
| 2013/0150633 | A1 | 6/2013 | Zhai et al. |

FOREIGN PATENT DOCUMENTS

| | | | |
|---|---|---|---|
| WO | 97/24307 | | 7/1997 |
| WO | WO 2008149011 | A2 * | 12/2008 |
| WO | WO 2011110889 | A1 * | 9/2011 |
| WO | 2011/135395 | A1 | 11/2011 |
| WO | 2012/052797 | A1 | 4/2012 |
| WO | 2012/066375 | A1 | 5/2012 |
| WO | 2012/166393 | A1 | 12/2012 |

OTHER PUBLICATIONS

PCT ISR & Written Opinion issued in PCT/US2014/059823 dated Dec. 16, 2014.

* cited by examiner

*Primary Examiner* — Jafar Parsa
*Assistant Examiner* — Medhanit Bahta
(74) *Attorney, Agent, or Firm* — Bruce O. Bradford

(57) ABSTRACT

This invention relates to methods and systems for producing hydrochlorofluoro-olefins, particularly 1-chloro-3,3,3-trifluoropropene (HCFO-1233zd) by the fluorination of a starting material selected from the group consisting of 1,1,1,3,3-pentachloropropane (HCC-240fa), 1,1,3,3-tetrachloropropene, and 1,1,1,3-tetrachloropropene, alone or in combination, in an ionic liquid.

16 Claims, No Drawings

PROCESS FOR PRODUCING 1-CHLORO-3,3,3-TRIFLUOROPROPENE IN AN IONIC LIQUID

CROSS-REFERENCE TO RELATED APPLICATIONS

This application claims domestic priority to commonly owned, copending U.S. Provisional Patent Application Ser. No. 61/891,184 filed Oct. 15, 2013, the disclosure of which is hereby incorporated herein by reference.

FIELD OF THE INVENTION

This invention relates to methods and systems for producing hydrochlorofluoro-olefins, particularly 1-chloro-3,3,3-trifluoropropene (HCFO-1233zd) by the fluorination of a starting material selected from the group consisting of 1,1,1,3,3-pentachloropropane (HCC-240fa), 1,1,3,3-tetrachloropropene, and 1,1,1,3-tetrachloropropene, alone or in combination, in an ionic liquid.

BACKGROUND OF THE INVENTION

Chlorofluorocarbon (CFC) based chemicals have been widely used in industry in a variety of different applications including as refrigerants, aerosol propellants, blowing agents and solvents, among others. However, certain CFCs are suspected of depleting the Earth's ozone layer. Accordingly, more environmentally friendly substitutes have been introduced as replacements for CFCs. For example, 1,1,1,3,3-pentafluoropropane (HFC-245fa) is recognized as having favorable physical properties for certain industrial applications, such as foam blowing agents and solvents, and therefore is consider to be a good substitute for the CFCs previously used for these applications. Unfortunately, the use of certain hydrofluorocarbons, including HFC-245fa, in industrial applications is now believed to contribute to the global warming. Accordingly, more environmentally friendly substitutes for hydrofluorocarbons are now being sought.

The compound 1-chloro-3,3,3-trifluoropropene, also known as HCFO-1233zd or simply 1233zd, is a candidate for replacing HFC-245fa in some applications, including uses as blowing agents and solvents. HCFO-1233zd has a cis or Z-isomer and a trans or E-isomer. Due to differences in the physical properties between these two isomers, pure 1233zd (E), pure 1233zd(Z), or certain mixtures of the two isomers may be suitable for particular applications as refrigerants, propellants, blowing agents, solvents, or for other uses.

Processes for synthesizing 1233zd are known. For example, WO 97/24307 discloses a process for preparing 1233zd via the gas-phase reaction of 1,1,1,3,3-penta-chloropropane (HCC-240fa) with hydrogen fluoride (HF). However, this process produces relatively low yields of 1233zd.

US Pub. No. 20120059199 discloses a non-catalyzed liquid phase reaction of HCC-240fa with HF to produce 1233zd. U.S. Pat. No. 6,844,475 describes a catalyzed liquid phase reaction of HCC-240fa with HF to produce 1233zd in higher yields. However the presence of the fluorination catalyst promotes the formation of heavy by-products, oligomers, and tars which build up in the reactor over time and lead to catalyst dilution and catalyst deactivation, resulting in loss of productivity due to excessive downtime to remove these by-products from the reactor on a periodic basis.

Accordingly, there remains a need for a process for producing 1233zd at high rates. This invention satisfies that need.

SUMMARY OF THE INVENTION

The present invention solves the problem faced by non-catalytic reactions for the production of HCFO-1233zd by conducting the fluorination of a starting material selected from the group consisting of 1,1,1,3,3-pentachloropropane (HCC-240fa), 1,1,3,3-tetrachloropropene, and 1,1,1,3-tetrachloropropene, alone or in combination, in the presence of an ionic liquid, which facilitates the dissolution and reaction between the starting materials and hydrogen fluoride (HF).

Thus, in one embodiment, the invention provides a process for the preparation of HCFO-1233zd which comprises:

(a) reacting a starting material selected from the group consisting of 1,1,1,3,3-pentachloropropane (HCC-240fa), 1,1,3,3-tetrachloropropene, and 1,1,1,3-tetrachloro-propene, alone or in combination, with anhydrous hydrogen fluoride in a liquid phase reactor in the presence of an ionic liquid, which has an anion selected from $I^-$, $Br^-$, $Cl^-$, $F^-$, $(HF)_nF^-$, wherein n=1.0-4.0, and their combinations, and a cation selected from ammonium, sulfonium, phosphonium, imidazolium, pyridinium, pyrrolidinium, thiazolium, triazolium, oxazolium, pyrazolium, and their combinations, with or without a catalyst, to produce a product stream comprising HCFO-1233zd (E), HCFO-1233zd(Z), HF, and HCl;

(b) optionally removing HCl produced by step (a);

(c) recovering HF present after step (b); and (d) recovering HCFO-1233zd(E), HCFO-1233zd(Z) or both from the result of step (c) by distillation.

In another embodiment, the present invention is directed to a process for the formation of 1-chloro-3,3,3-trifluoropropene (HCFO-1233zd) comprising reacting a starting material selected from the group consisting of 1,1,1,3,3-pentachloropropane (HCC-240fa), 1,1,3,3-tetrachloropropene, and 1,1,1,3-tetrachloropropene, alone or in combination, with hydrogen fluoride in a liquid phase reactor in the presence of an ionic liquid.

In certain embodiments, the starting material comprises 1,1,1,3,3-pentachloro-propane (HCC-240fa). In certain embodiments, the starting material comprises 1,1,3,3-tetrachloropropene. In certain embodiments, the starting material comprises 1,1,1,3-tetrachloropropene. In certain embodiments, the starting material comprises a mixture of two or three of the starting materials selected from the group consisting of 1,1,1,3,3-pentachloro-propane (HCC-240fa), 1,1,3,3-tetrachloropropene, and 1,1,1,3-tetrachloro-propene.

In certain embodiments, the hydrogen fluoride is anhydrous.

In certain embodiments, the ionic liquid comprises an anion selected from the group consisting of $I^-$, $Br^-$, $Cl^-$, $F^-$, $(HF)_nF^-$, wherein n=1.0-4.0, and combinations thereof. In certain embodiments, the anions in the ionic liquid are externally introduced into the process. In certain embodiments, the anions in the ionic liquid are in-situ generated. In certain embodiments, the anion $(HF)_nF^-$, wherein n=1.0-4.0, is formed by the interactions of an ionic liquid with $Cl^-$ as anion and HF in the reactor.

In certain embodiments, the ionic liquid comprises a cation selected from the group consisting of ammonium, sulfonium, phosphonium, imidazolium, pyridinium, pyrrolidinium, thiazolium, triazolium, oxazolium, pyrazolium, and combinations thereof. In certain embodiments, the ionic liquid comprises an imidazolium cation selected from the group consisting of 1-methylimidazolium, 1-ethyl-imidazolium, 1-propylimidazolium, 1-butylimidazolium, 1,2-dimethylimidazolium, 1,3-dimethylimidazolium, 1-ethyl-3-methylimidazolium, 1-n-butyl-3-methylimidazolium, 1-n-butyl-3-ethylimidazolium, 1,3-di-n-butylimidazolium, 1-methyl- 3-octylimidazolium, 1-decyl-3-methylimidazolium, 3-butyl-1-methylimidazolium, 3-butyl-1-ethyl-imidazolium, 3-methyl-2-ethylimidazolium, 3-butyl-2-methylimidazolium, 3-butyl-2-ethyl-imidazolium, 3,4-dimethylimidazolium, 3-butyl-4-methylimidazolium, 1,2,3-trimethyl-imidazolium, 1-butyl-2,3-dimethyl-imidazolium, 1,3-dibutyl-2-methylimidazolium, 3-butyl-1,2-dimethylimidazolium, 1,3,4-trimethylimidazolium, 3-butyl-1,4-dimethyl-imidazolium, 2-ethyl-3,4-dimethyl-imidazolium, 3-butyl-2-ethyl-4-methylimidazolium, 1,3,4,5-tetramethylimidazolium, 3-butyl-1,4,5-trimethylimidazolium, and combinations thereof.

In certain embodiments, the amount of ionic liquid used relative to the amount of starting material present is from about 0.001 to about 10 mol %. In certain embodiments, the amount of ionic liquid used relative to the amount of starting material present is from about 0.01 to about 5 mol %. In certain embodiments, the amount of ionic liquid used relative to the amount of starting material present is from about 0.05 to about 5 mol %.

While not wishing to be bound by theory, the ionic liquids (anions and cations) defined herein have been selected in view of their compatibility with HF. The reactions of the present invention are believed to function because the selected ionic liquids allow the reactants to mix together, which they otherwise do not because 240fa and HF are not soluble each other. The use of the selected ionic liquids is believed to promote the reaction because these ionic liquids facilitate the dissolution between 240fa (and other organic reactant as well) and HF.

In certain embodiments, a fluorination catalyst is employed in the reaction. In certain embodiments, the catalyst is selected from Lewis acid catalysts. In certain embodiments, the Lewis acid catalyst is selected from the group consisting of $TiCl_4$, $SnCl_4$, $SbCl_5$, $TaCl_5$, $AlCl_3$, $FeCl_3$, and combinations thereof. In certain embodiments, the catalyst comprises $TiCl_4$. In certain embodiments, the fluorination reaction is conducted without a catalyst In certain embodiments, the fluorination reaction is conducted in an agitated liquid phase fluorination reactor in a continuous mode. In certain embodiments, the fluorination reaction is conducted in an agitated liquid phase fluorination reactor in a semi-batch mode.

In certain embodiments, the mole ratio of HF to starting material ranges from 3:1 to 30:1. In certain embodiments, the mole ratio of HF to starting material ranges from 5:1 to 20:1. In certain embodiments, the mole ratio of HF to starting material ranges from 10:1 to 15:1.

In certain embodiments, the reaction temperature range is from 50° C. to 200° C. In certain embodiments, the reaction temperature range is from 80° C. to 160° C. In certain embodiments, the reaction temperature range is from 90° C. to 150° C.

Another embodiment of the present invention is a process for the formation of 1-chloro-3,3,3-trifluoropropene (HCFO-1233zd) comprising the following steps:

(a) fluorination of a starting material selected from the group consisting of 1,1,1,3,3-pentachloropropane (HCC-240fa), 1,1,3,3-tetrachloropropene, and 1,1,1,3-tetrachloropropene, alone or in combination, using HF in the presence of an ionic liquid, with simultaneous removal of by-product HCl and the product 1233zd(E+Z);

(b) separation and purification of by-product HCl;

(c) separation of excess HF back to step (a); and (d) purification of final product, 1233zd(E), 1233zd(Z), or a mixture of these two isomers.

In certain embodiments, step (a) is conducted in a continuous mode. In certain embodiments, step (a) is conducted in a semi-batch mode. In certain embodiments, step (a) is conducted with a catalyst. In certain embodiments, step (a) is conducted without a catalyst.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

DETAILED DESCRIPTION OF THE INVENTION

The present invention can be generally described as a new process for producing 1233zd, in which a starting material selected from the group consisting of 1,1,1,3,3-pentachloropropane (HCC-240fa), 1,1,3,3-tetrachloropropene, and 1,1,1,3-tetrachloro-propene, alone or in combination, is fluorinated with anhydrous HF in the presence of an ionic liquid, with or without a catalyst, under conditions effective to produce (E) 1-chloro-3,3,3-trifluoropropene (1233zd(E))/(Z) 1-chloro-3,3,3-trifluoropropene (1233zd(Z)) plus HCl as a by-product.

In certain embodiments, a preferred starting material comprises 1,1,1,3,3-pentachloropropane (HCC-240fa). In certain embodiments, a preferred starting material comprises 1,1,3,3-tetrachloropropene. In certain embodiments, a preferred starting material comprises 1,1,1,3-tetrachloropropene. In certain embodiments, a preferred starting material comprises a mixture of two or three of these starting materials.

An ionic liquid (IL) is a salt in the liquid state. In some contexts, the term has been restricted to salts whose melting point is below some arbitrary temperature, such as 100° C. While ordinary liquids such as water and gasoline are predominantly made of electrically neutral molecules, ionic liquids are largely made of ions and short-lived ion pairs. These substances are variously called liquid electrolytes, ionic melts, ionic fluids, fused salts, liquid salts, or ionic glasses. For purposes of the present invention, an ionic liquid is a substance that facilitates the dissolution and reaction between organic reactant and HF.

The anion included in the ionic liquid is selected from $I^-$, $Br^-$, $Cl^-$, $F^-$, $(HF)_nF^-$ (n=1.0-4.0), and their combinations. The anions can be externally introduced into the process or in-situ generated. For instance, $(HF)_nF^-$, wherein n=1.0-4.0, can be formed from the interactions of an ionic liquid with $Cl^-$ as anion and HF in the reactor.

The cation included in the ionic liquid is selected from ammonium, sulfonium, phosphonium, imidazolium, pyridinium, pyrrolidinium, thiazolium, triazolium, oxazolium, pyrazolium, and their combinations. Preferred cations include ammonium, phosphonium, imidazolium, pyridinium, pyrrolidinium, and their combinations. More preferred cations include imidazolium, pyridinium, pyrrolidinium, and their combinations. The most preferred cation is imidazolium. Non-limiting examples of imidazolium include, but are not limited to, 1-methylimidazolium, 1-ethylimidazolium, 1-propylimidazolium, 1-butylimidazolium, 1,2-dimethylimidazolium, 1,3-dimethylimidazolium, 1-ethyl-3-methylimidazolium, 1-n-butyl-3-methylimidazolium, 1-n-butyl-3-ethylimidazolium, 1,3-di-n-butylimidazolium, 1-methyl-3-octylimidazolium, 1-decyl-3-methylimidazolium, 3-butyl-1-methylimidazolium, 3-butyl-1-ethylimidazolium, 3-methyl-2-ethylimidazolium, 3-butyl-2-methylimidazolium, 3-butyl-2-ethyl-imidazolium, 3,4-dimethylimidazolium, 3-butyl-4-methylimidazolium, 1,2,3-trimethyl-imidazolium, 1-butyl-2,3-dimethylimidazolium, 1,3-dibutyl-2-methylimidazolium, 3-butyl-1,2-dimethylimidazolium, 1,3,4-trimethylimidazolium, 3-butyl-1,4-dimethyl-imidazolium, 2-ethyl-3,4-dimethylimidazolium, 3-butyl-2-ethyl-4-methylimidazolium, 1,3,4,5-tetramethylimidazolium, 3-butyl-1,4,5-trimethylimidazolium, and their combinations. For the same type of cation, cations with more alkyl groups and longer alkyl group are more preferred.

An effective amount of the ionic liquid should be used in order to effect the desired reaction; such an amount can be determined by limited experimentation once the reactants, process conditions and ionic liquid are selected. Typically, the amount of ionic liquid used relative to the amount of the starting material present is from about 0.001 to about 10 mol %; for example from about 0.01 to about 5 mol %; alternatively, for example from about 0.05 to about 5 mol %.

In certain embodiments, the catalyst choices are selected from known Lewis acid catalysts. The preferred catalysts are $TiCl_4$, $SnCl_4$, $SbCl_5$, $TaCl_5$, $AlCl_3$, or $FeCl_3$, with $TiCl_4$ being more preferred. In certain embodiments, the most preferred choice is operation of the reactor without employing any catalyst.

The fluorination reaction can be accomplished in an agitated liquid phase fluorination reactor. Required amounts of an ionic liquid, HF and a starting material such as HCC-240fa, can be charged to the fluorination reactor and the reaction can be initiated immediately upon heating to the desired reaction temperature while maintaining agitation. After that, continuous flows of HF and starting material to the fluorination reactor can be started immediately to cause continuous reaction. The mole ratio of HF to starting material may range from 3:1 to 30:1, preferably from 5:1 to 20:1, and more preferably from 10:1 to 15:1.

Alternatively, the starting material, such as HCC-240fa, and an ionic liquid can be added as batch charges, and then HF can be added gradually to the reactor (i.e., a semi-batch operation). Alternatively, HF and an ionic liquid can be added as batch charges, and then the starting material can be added gradually to the reactor (also a semi-batch operation).

It has been discovered that maintaining the reaction under the operating conditions, particularly, a temperature range of 50° C. to 200° C., more preferably 80° C. to 160° C., and most preferably 90° C. to 150° C., produces a high ratio of 1233zd (E) to 1233zd(Z).

While there is no particular restriction as to the reaction pressure, in other words the reaction may be conducted under atmospheric pressure or under an elevated pressure, it may be necessary to operate at elevated pressure if it is desired to maintain the bulk of HF, the starting material, such as HCC-240fa, plus partially fluorinated intermediates (e.g., 1,1,3,3-tetrachloro-1-fluoropropane (241fa), 1,3,3-trichloro-3-fluoropropene (1231zd), 1,3,3-trichloro-1,1-difluoropropane (242fa), 1,3-dichloro-3,3-difluoro-propene (1232zd), 1,1-dichloro-3,3,3-trifluoropropane (243fa)) in the liquid state, at least during the reaction. When the reaction is conducted under elevated pressure, useful pressures are from about 0 to about 600 psig. In certain embodiments, a more preferred pressure range is from 200 psig to 500 psig and a most preferred pressure range is from 300 psig to 450 psig.

In certain embodiments, the manufacturing process comprises four major unit operations. These operation units and/or the reactions therein, comprise: (1) fluorination reaction of the starting material, such as HCC-240fa (in continuous or semi-batch mode) using HF in the presence of an ionic liquid, with or without a catalyst, with simultaneous removal of by-product HCl and the product 1233zd(E+Z), (2) separation and purification of by-product HCl, (3) separation of excess HF back to (1), and (4) purification of final product, 1233zd (E), 1233zd(Z), or a mixture of these two isomers.

In the practice of the present invention, the reactor is constructed from materials which are resistant to the corrosive effects of the HF and HCl, such as Hastelloy-C, Inconel, Monel, Incalloy, or fluoropolymer-lined steel vessels. The reactor is equipped with an agitator. Such liquid-phase fluorination reactors are well known in the art. The reactor is further equipped with an optional rectifying column which permits the desired product to leave (along with by-product HCl, traces of over-fluorinated by-products (e.g., 244fa, 1234ze(E+Z), 245fa, etc.) and sufficient anhydrous hydrogen fluoride (AHF) to form azeotropes), while retaining the bulk of the HF, plus partially fluorinated intermediates (e.g., 241fa, 1231zd, 242fa, 1232zd, and 243fa, etc.). The rectifying column is a packed pipe equipped with a condenser and this step is conducted by adjusting the temperature of the condenser to a range of from about 20° C. to about 100° C. Proper temperature control of the coolant and sufficient reflux action are desirable for optimum operation of the rectifying column to be effective.

General operating conditions which we have found to work well for the reaction and optional rectifying column are: Operating pressure of 100 to 500 psig maintained by a control valve on the exiting flow from the rectifying column; reactor temperature of 60° C. to 180° C., primarily supplied by steam flow into the reactor jacket; application of −40° C. to 35° C. brine cooling to the heat exchanger on top of the rectifying column to induce reflux; temperature in the center portion of the stripper about 5° C. to 60° C. below that in the reactor; additional heat input by superheating the HF feed with high-pressure steam to 70° C. to 180° C.

The gaseous stream exiting the top of reactor or optional rectifying column attached to the fluorination reactor comprising mainly 1233zd(E), 1233zd(Z), HF, and HCl (with some minor components including unconverted starting material, such as 240fa, partially fluorinated intermediates/by-products, over-fluorinated by-products) is then optionally, but preferably, fed to an HCl distillation column to remove relatively pure HCl from the reaction mixture. The pressure of the HCl column is preferred to match that of the reactor. The HCl can then be purified and collected for sale (or further purification) by using a low-temperature HCl distillation column. Alternatively, high purity HCl is isolated and absorbed in de-ionized water as concentrated HCl aqueous solution for sale.

The essentially HCl free organic/HF mixture exiting the HCl column is optionally fed to a distillation column to remove heavy reaction products before the resulting mixture enters a sulfuric acid absorber. The pressure of this column is preferably maintained at from about 200 psig or less, more preferably from about 150 psig or less and most preferably from about 100 psig or less. The overhead of the distillation column contains HCFO-1233zd(E), HCFO-1233zd(Z), traces of light organics, e.g., 1234ze(E+Z) and anhydrous hydrogen fluoride in the amount greater than that needed to form the azeotropes. The bottom cuts of the distillation column contain recyclable and non-recyclable heavies. The recyclable heavies such as 240fa, 241fa, 1231zd, 242fa, 1232zd, and 243fa are recycled back to the fluorination reactor. The non-recyclable heavies are disposed of.

In certain embodiments, the essentially HCl free organic/HF mixture is fed to a sulfuric extractor or a phase separator for removal of HF from this mixture. HF is either dissolved in the sulfuric acid or phase separated from the organic mixture. For embodiments utilizing a sulfuric acid adsorption system, sulfuric acid is preferably added such that the weight ratio of sulfuric acid to hydrogen fluoride ranges from about 1:1 to about 10:1. More preferably the weight ratio ranges from about 1:1 to about 8:1 and most preferably from about 2:1 to about 4:1. The HF is then desorbed from the sulfuric acid/HF mixture by stripping distillation and recycled back to the fluorination reactor.

For embodiments utilizing a phase separator, preferably the extraction is conducted at a temperature of from about −20° C. to about 100° C., more preferably from about −10° C. to about 60° C., and most preferably from about 0° C. to about 40° C. The HF is then phase-separated and recycled back to the fluorination reactor. The organic mixture either from the overhead of the sulfuric acid extractor or from the bottom layer of the phase separator may require treatment (scrubbing or adsorption) to remove traces of HF before it is sent to next unit operation for product isolation.

In certain embodiments, the isomers 1233zd(E) and 1233zd(Z) are isolated as two products. Acid free crude product is first sent to a distillation column, from which 1233zd(E) exits the top of the column together with some light components having lower boiling points than 1233zd(E) while 1233zd(Z) exits from the bottom of the column together with some heavy components having higher boiling points than 1233zd(Z). The overhead stream and the bottom stream are then sent to two separate columns for further purification to obtain 1233zd(E) and 1233zd(Z) products.

The following examples are provided to further illustrate the invention and should not be taken as limitations of the invention.

EXAMPLE 1

HCC-240fa Fluorination in the Presence of an Ionic Liquid

A one gallon agitated Hastelloy-C Parr reactor is used and the reaction is run in a batch mode. 300 grams of AHF and 250 grams of HCC-240fa (1,1,1,3,3-pentachloro-propane) (13.0 to 1 mole ratio HF:240fa) as well as 6 grams of EMIm(HF)$_{2.3}$F (EMIm refers to 1-ethyl-3-methyl imidazolium) ionic liquid (about 3.0 mol % with respect to the amount of 240fa) are charged to the reactor at room temperature. The agitator is then turned on ensuring the reactor contents are well mixed. Then the reactor is heated to the desired temperature. Upon heating the pressure begins to rise as HCl by product is produced as a result of a fluorination reaction. The reactor is heated to about 110° C. over a period of several hours and holds at that temperature. The pressure is controlled in the range of 275 psig to 350 psig by venting off the HCl generated in the reaction to a dry-ice trap (DIT).

Upon the completion of the reaction after about 8 hrs. (determined by lack of HCl generation), the pressure from the reactor is vented into the DIT. The crude product from the DIT is transferred into a 1 L Monel absorption cylinder (frozen in dry-ice) with about 400 grams of water. The absorption cylinder is allowed to warm up to room temperature and a sample of an organic layer that has formed in the cylinder (aqueous and organic layers are present in the cylinder upon discharge) is taken and analyzed by gas chromatography (GC). GC results show 3.0 GC % 245fa, 93.0 GC % 1233zd (E), 0.2 GC % 244fa, 3.0 GC % 1233zd(Z). The amount of organic collected is later quantified by further analysis of the different phases to be about 80 grams.

The organic remaining in the reactor after venting is recovered by quenching the reactor with about 400 grams of water to absorb HF and HCl, and then adding about 100 grams of carbon tetrachloride. The reactor is then opened and its contents are discharged into a plastic bottle. The organic is separated from the aqueous phase by use of a reparatory funnel. The amount of heavies collected from the reactor is calculated by subtracting the weight of $CCl_4$ added to the reactor from the total weight of organic phase collected to be about 100 grams. GC/MS and GC analyses of the organic layer reveal three distinct peaks attributed to under-fluorinated species HCFC-241fa, 94.0 GC %, HCFC-242fa, 2.0 GC %, and the starting material HCC-240fa, 4.0 GC %.

EXAMPLE 2

HCC-240fa Fluorination in the Presence of an Ionic Liquid

All conditions are the same as in Example 1 except that 6 g of EMIm(HF)F (EMIm refers to 1-ethyl-3-methyl imidazolium) ionic liquid is used. The reaction is conducted in the same Parr reactor and following the same procedure as described in Example 1.

Upon the completion of the reaction after about 8 hrs. (determined by lack of HCl generation), the pressure from the reactor is vented into the DIT. The crude product from the DIT is transferred into a 1 L Monel absorption cylinder (frozen in dry-ice) with about 400 grams of water. The absorption cylinder is allowed to warm up to room temperature and a sample of an organic layer that has formed in the cylinder (aqueous and organic layers are present in the cylinder upon discharge) is taken and analyzed by gas chromatography (GC). GC results show 2.5 GC % 245fa, 93.3 GC % 1233zd (E), 0.2 GC % 244fa, 3.2 GC % 1233zd(Z). The amount of organic collected is later quantified by further analysis of the different phases to be about 80 grams.

The organic remaining in the reactor after venting is recovered by quenching the reactor with about 400 grams of water to absorb HF and HCl, and then adding about 100 grams of carbon tetrachloride. The reactor is then opened and its contents are discharged into a plastic bottle. The organic is separated from the aqueous phase by use of a reparatory funnel. The amount of heavies collected from the reactor is calculated by subtracting the weight of $CCl_4$ added to the reactor from the total weight of organic phase collected to be about 100 grams. GC/MS and GC analyses of the organic layer reveal three distinct peaks attributed to under-fluorinated species HCFC-241fa, 94.3 GC %, HCFC-242fa, 2.2 GC %, and the starting material HCC-240fa, 3.5 GC %.

EXAMPLE 3

HCC-240fa Fluorination in the Presence of an Ionic Liquid

All conditions are the same as in Example 1 except that 6 g of EMImCl (EMIm refers to 1-ethyl-3-methyl imidazolium) ionic liquid is used. The reaction is conducted in the same Parr reactor and following the same procedure as described in Example 1.

Upon the completion of the reaction after about 8 hrs. (determined by lack of HCl generation), the pressure from the reactor is vented into the DIT. The crude product from the DIT is transferred into a 1 L Monel absorption cylinder (frozen in dry-ice) with about 400 grams of water. The absorption cylinder is allowed to warm up to room temperature and a sample of an organic layer that has formed in the cylinder (aqueous and organic layers are present in the cylinder upon discharge) is taken and analyzed by gas chromatography (GC). GC results show 3.2 GC % 245fa, 92.8 GC % 1233zd (E), 0.3 GC % 244fa, 3.1 GC % 1233zd(Z). The amount of organic collected is later quantified by further analysis of the different phases to be about 80 grams.

The organic remaining in the reactor after venting is recovered by quenching the reactor with about 400 grams of water to absorb HF and HCl, and then adding about 100 grams of carbon tetrachloride. The reactor is then opened and its contents are discharged into a plastic bottle. The organic is separated from the aqueous phase by use of a reparatory funnel. The amount of heavies collected from the reactor is calculated by subtracting the weight of $CCl_4$ added to the reactor from the total weight of organic phase collected to be about 100 grams. GC/MS and GC analyses of the organic layer reveal three distinct peaks attributed to under-fluorinated species HCFC-241fa, 93.7 GC %, HCFC-242fa, 2.3 GC %, and the starting material HCC-240fa, 4.2 GC %.

COMPARATIVE EXAMPLE 1

HCC-240fa Fluorination in the Absence of an Ionic Liquid

The experiment uses the same one gallon agitated Hastelloy-C Parr reactor as described in Example 1 and is run in a batch mode as well. 300 grams of AHF and 250 grams of HCC-240fa (1,1,1,3,3-pentachloropropane) (13.0 to 1 mole ratio HF:240fa) are charged to the reactor at room temperature. The agitator is then turned on ensuring the reactor contents are well mixed. Then the reactor is heated to the desired temperature. Upon heating the pressure begins to rise as HCl by product is produced as a result of a fluorination reaction. The reactor is heated to about 110° C. over a period of several hours and holds at that temperature. The pressure is controlled in the range of 275 psig to 350 psig by venting off the HCl generated in the reaction to a dry-ice trap (DIT).

Upon the completion of the reaction after about 10 hrs. (determined by lack of HCl generation), the pressure from the reactor is vented into the DIT. The crude product from the DIT is transferred into 1 L Monel absorption cylinders (frozen in dry-ice) with about 400 grams of water. The absorption cylinder is allowed to warm up to room temperature and a sample of an organic layer that has formed in the cylinder (aqueous and organic layers are present in the cylinder upon discharge) is taken and analyzed by gas chromatography (GC). GC results show 4.5 GC % 245fa, 90.6 GC % 1233zd (E), 0.2 GC % 244fa, 2.9 GC % 1233zd(Z). The amount of organic collected is later quantified by further analysis of the different phases to be about 75 grams.

The organic remaining in the reactor after venting is recovered by quenching the reactor with about 400 grams of water to absorb HF and HCl, and then adding about 100 grams of carbon tetrachloride. The reactor is then opened and its contents are discharged into a plastic bottle. The organic is separated from the aqueous phase by use of a reparatory funnel. The amount of heavies collected from the reactor is calculated by subtracting the weight of $CCl_4$ added to the reactor from the total weight of organic phase collected to be about 100 grams. GC/MS and GC analyses of the organic layer reveal three distinct peaks attributed to under-fluorinated species HCFC-241fa, 91.0 GC %, HCFC-242fa, 0.8 GC %, and the starting material HCC-240fa, 8.2 GC %.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for the formation of 1-chloro-3,3,3- trifluoropropene (HCFO-1233zd) comprising reacting a starting material selected from the group consisting of 1,1,1,3,3-pentachloropropane (HCC-240fa), 1,1,3,3-tetrachloropropene, 1,1,1,3-tetrachloropropene, and mixtures thereof, with hydrogen fluoride in a liquid phase reactor in a reaction medium consisting essentially of HF, the starting material, and an ionic liquid without a catalyst.

2. The process of claim 1, wherein the starting material comprises 1,1,1,3,3-pentachloropropane (HCC-240fa).

3. The process of claim 1, wherein the starting material comprises 1,1,3,3-tetrachloropropene.

4. The process of claim 1, wherein the starting material comprises 1,1,1,3-tetrachloropropene.

5. The process of claim 1, wherein the starting material comprises a mixture of two or three of the starting materials selected from the group consisting of 1,1,1,3,3-pentachloropropane (HCC-240fa), 1,1,3,3-tetrachloropropene, and 1,1,1,3-tetrachloro-propene.

6. The process of claim 1, wherein the hydrogen fluoride is anhydrous.

7. The process of claim 1, wherein the ionic liquid comprises an anion selected from the group consisting of $I^-$, $Br^-$, $Cl^-$, $F^-$, $(HF)_nF^-$, wherein n=1.0-4.0, and combinations thereof.

8. The process of claim 7, wherein the anions in the ionic liquid are externally introduced into the process.

9. The process of claim 7, wherein the anions in the ionic liquid are in-situ generated.

10. The process of claim 7, wherein the anion $(HF)_nF^-$, wherein n=1.0 -4.0, is formed by the interactions of an ionic liquid with $Cl^-$ as anion and HF in the reactor.

11. The process of claim 1, wherein the ionic liquid comprises a cation selected from the group consisting of ammonium, sulfonium, phosphonium, imidazolium, pyridinium, pyrrolidinium, thiazolium, triazolium, oxazolium, pyrazolium, and combinations thereof.

12. The process of claim 1, wherein the ionic liquid comprises an imidazolium cation selected from the group consisting of 1-methylimidazolium, 1-ethyl -imidazolium,1-propylimidazolium, 1-butylimidazolium, 1,2- dimethylimidazolium, 1,3-dimethylimidazolium, 1-ethyl-3-methylimidazolium, 1-n-butyl-3-methylimidazolium, 1-n-butyl-3-ethylimidazolium, 1,3-di-n-butylimidazolium, 1-methyl-3-octylimidazolium, 1-decyl-3-methylimidazolium, 3-butyl-1-methylimidazolium, 3-butyl1-ethyl-imidazolium, 3-methyl-2-ethylimidazolium, 3-butyl-2-methylimidazolium, 3-butyl-2-ethyl-imidazolium, 3,4-dimethylimidazolium, 3-butyl-4-methylimidazolium, 1,2,3-trimethyl-imidazolium, 1-butyl-2,3-dimethylimidazolium, 1,3-dibutyl-2-methylimidazolium,3-butyl-1,2-dimethylimidazolium, 1,3,4-trimethylimidazolium, 3-butyl-1,4-dimethyl-imidazolium, 2-ethyl-3,4-dimethylimidazolium, 3-butyl-2-ethyl-4-methylimidazolium,1,3,4,5-tetramethylimidazolium, 3-butyl-1,4,5-trimethylimidazolium, and combinations thereof.

13. The process of claim 1, wherein the amount of ionic liquid used relative to the amount of starting material present is from about 0.001 to about 10 mol %.

14. The process of claim 1, wherein the mole ratio of HF to starting material ranges from 3:1 to 30:1.

15. The process of claim 1, wherein the reaction temperature range is from 50° C. to 200° C.

16. A process for the formation of 1-chloro-3,3,3-trifluoropropene (HCFO-1233zd) comprising the following steps:

(a) fluorination of a starting material selected from the group consisting of 1,1,1,3,3-pentachloropropane (HCC-240fa), 1,1,3,3-tetrachloropropene, 1,1,1,3-tetrachloropropene, and mixtures thereof, using HF in a reaction medium consisting essentially of HF, the starting material and an ionic liquid without a catalyst, with simultaneous removal of by-product HCl and the product 1233zd(E+Z);

(b) separation and purification of by-product HCl;

(c) separation of excess HF back to step (a); and (d) purification of final product, 1233zd(E), 1233zd(Z), or a mixture of these two isomers.

* * * * *